(12) United States Patent
Tonani et al.

(10) Patent No.: US 9,668,947 B2
(45) Date of Patent: Jun. 6, 2017

(54) WIPE FOR APPLICATION OF AT LEAST ONE ACTIVE PRINCIPLE ON THE SKIN

(75) Inventors: Alberto Tonani, Casanova Elvo (IT); Andrea Novello, Cossato (IT); Erika Favero, Bricherasio (IT); Valerio Favero, Pinerolo (IT)

(73) Assignees: Zanolo S.p.A., Arborio (VC) (IT); Turati Idrofilo S.p.A., Luserna San Giovanni (TO) (IT)

( * ) Notice: Subject to any disclaimer, the term of this patent is extended or adjusted under 35 U.S.C. 154(b) by 313 days.

(21) Appl. No.: 13/993,984

(22) PCT Filed: Jun. 26, 2012

(86) PCT No.: PCT/IB2012/053221
§ 371 (c)(1),
(2), (4) Date: Jun. 13, 2013

(87) PCT Pub. No.: WO2013/014549
PCT Pub. Date: Jan. 31, 2013

(65) Prior Publication Data
US 2013/0266624 A1    Oct. 10, 2013

(30) Foreign Application Priority Data

Jul. 28, 2011  (IT) .............................. TO2011A0690

(51) Int. Cl.
| A61K 8/02 | (2006.01) |
| A61Q 19/00 | (2006.01) |
| A61K 8/11 | (2006.01) |
| A61K 8/44 | (2006.01) |
| A61K 8/67 | (2006.01) |
| A61K 8/87 | (2006.01) |
| A61K 8/92 | (2006.01) |
| A61K 8/97 | (2017.01) |

(52) U.S. Cl.
CPC .............. *A61K 8/0208* (2013.01); *A61K 8/11* (2013.01); *A61K 8/442* (2013.01); *A61K 8/678* (2013.01); *A61K 8/87* (2013.01); *A61K 8/922* (2013.01); *A61K 8/97* (2013.01); *A61Q 19/00* (2013.01); *A61K 2800/31* (2013.01); *A61K 2800/412* (2013.01)

(58) Field of Classification Search
None
See application file for complete search history.

(56) References Cited

U.S. PATENT DOCUMENTS

| 4,748,991 | A  * | 6/1988 | Hofman et al. .............. 132/320 |
| 6,784,145 | B2 * | 8/2004 | Delambre et al. ............ 510/130 |
| 7,597,780 | B2 * | 10/2009 | Buder et al. ................ 162/164.4 |
| 2004/0241333 | A1 | 12/2004 | Cielenski et al. |
| 2005/0158369 | A1 * | 7/2005 | Dorschner et al. ............ 424/443 |
| 2006/0270585 | A1 * | 11/2006 | Jordan et al. ................. 510/439 |
| 2007/0042182 | A1 * | 2/2007 | Markus et al. ............ 428/402.2 |
| 2007/0071537 | A1 | 3/2007 | Reddy et al. |
| 2008/0193399 | A1 * | 8/2008 | Alleon ........................... 424/61 |

FOREIGN PATENT DOCUMENTS

| EP | 0 247 864 A2 | 12/1987 |
| EP | 0 445 914 | 9/1991 |
| FR | 2 829 929 | 3/2003 |
| FR | 2 829 929 A1 | 3/2003 |
| FR | 2 858 637 | 2/2005 |
| JP | 63-27417 A | 2/1988 |
| JP | 1-143811 A | 6/1989 |
| JP | 2-36114 A | 2/1990 |
| JP | 2-200876 A | 8/1990 |
| JP | 3-78094 A | 8/1991 |
| JP | 7-100368 A | 4/1995 |
| JP | 9-67230 A | 3/1997 |
| JP | 3102807 U | 4/2004 |
| JP | 2008-188072 A | 8/2008 |
| WO | WO 00/70009 | 11/2000 |
| WO | WO 01/35905 | 5/2001 |

OTHER PUBLICATIONS

Wikipedia Polysorbate 80, (accessed Mar. 17, 2015), pp. 1-4.*
BASF, L-menthol FCC, acessed Mar. 17, 2015, pp. 1-4.*
Britannica, Lipophilicity Chemistry, (Apr. 30, 2008) pp. 1-3.*
Wang, Jun-Hua, Journal of Donghua Universtiy (Eng. Ed.) vol. 24. No. 3 (2007) pp. 337-340.*
Dow, Toluene Diisocyanate, (Nov. 28, 2010) pp. 1-8).*
FR2829929, Machine Translation, (Mar. 28, 2003), Dhulst, Jerome, et al., pp. 1-11.*
Rupp, Jurg, Spunlaced or Hydroentangled Nonwovens, Textile World (Jul./Aug. 2008) pp. 1-3.*
International Search Report for PCT/IB2012/053221 mailed Nov. 5, 2012.
Written Opinion of the International Searching Authority mailed Nov. 5, 2012.
Notice of Reasons for Rejection dated Jan. 5, 2016, issued in Japanese Patent Application No. 2014-522173 and English translation.

* cited by examiner

*Primary Examiner* — Dennis J Parad
*Assistant Examiner* — Lyndsey Beckhardt
(74) *Attorney, Agent, or Firm* — Nixon & Vanderhye P.C.

(57) ABSTRACT

Dry wipe for application of at least one active principle on the skin, including: an inert laminar support; a plurality of microcapsules applied to the inert laminar support, the microcapsules containing at least one active principle; at least one surfactant applied to the inert laminar support.

15 Claims, No Drawings

WIPE FOR APPLICATION OF AT LEAST ONE ACTIVE PRINCIPLE ON THE SKIN

This application is the U.S. national phase of International Application No. PCT/IB2012/053221 filed 26 Jun. 2012 which designated the U.S. and claims priority to IT TO2011A000690 filed 28 Jul. 2011, the entire contents of each of which are hereby incorporated by reference.

FIELD OF THE INVENTION

The present description concerns wipes for the application of an active principle, preferably a cosmetic active principle, on the skin. In particular, the present description concerns a wipe in the form of an absorbent cotton sheet for the application of a cosmetic active principle on the skin.

TECHNICAL BACKGROUND

The known wipes for skin care are wet wipes, i.e., wipes impregnated with the active principle for the treatment of skin in a liquid form, or dissolved in a solvent phase.

Such wipes must be packaged in sealed packages to prevent evaporation of the liquid phase and allow their use over time. The wipes may be packaged in single or multiple packages; in the first case the package must be sealed at the time of industrial production, while in the second case, the package must be suitable for opening and reclosing in a hermetically sealed manner to ensure preservation of the necessary degree of humidity in the wipes for their use over time.

However, very often such packages are not properly sealed or are not able to maintain the necessary seal so that at the moment of use the user extracts a wipe from the package that is dry and no longer usable.

Therefore, the need is felt to develop wipes that do not require such special packaging.

SUMMARY OF THE INVENTION

Considering these premises, the need is felt for solutions that allow the realization of wipes for application of an active principle on the skin, preferably but not necessarily a cosmetic active principle, that do not need to be packaged in hermetically sealed packages.

According to the invention, the above object is achieved by means of the solution specifically recalled in the attached claims, which constitute an integral part of the present description.

One embodiment of the present invention concerns a dry wipe for application of an active principle, preferably cosmetic, on the skin in which the active principle is contained in microcapsules applied on the surface of the wipe and wherein the wipe contains at least one surfactant.

A particularly preferred embodiment concerns a dry wipe for application of an active principle on the skin, where the wipe comprises an inert laminar support, preferably a sheet of nonwoven absorbent cotton fabric, a plurality of microcapsules containing the at least one active principle, preferably lipophilic, and at least one surfactant, the microcapsules and the surfactant being applied on the surface of the laminar support.

DETAILED DESCRIPTION OF THE INVENTION

In the description that follows, numerous specific details are presented to provide a thorough understanding of the embodiments. The embodiments can be practiced without one or more of the specific details, or with other methods, components, materials, etc. In other instances, well-known structures, materials or operations are not shown or described in detail to avoid obscuring certain aspects of the embodiments.

Reference throughout the present specification to "one embodiment" or "an embodiment" means that a particular feature, structure or characteristic described in connection with the embodiment is included in at least one embodiment. Thus, the phrase "in one embodiment" or "in an embodiment" in various places throughout the present description are not necessarily all referring to the same embodiment. Furthermore, the details of features, structures, or characteristics may be combined in any suitable manner in one or more embodiments.

The headings provided herein are for convenience only and do not interpret the scope or meaning of the embodiments.

As mentioned above, the present invention has the object of developing wipes for the application of an active principle, preferably but not necessarily a cosmetic active principle, on the skin that do not need to be packaged hermetically sealed in order to preserve the function, i.e., the necessary degree of humidity, of the wipes themselves.

One embodiment of the present invention, concerns a dry wipe for the application of at least one active principle on the skin, wherein the at least one active principle is contained in microcapsules applied on the surface of the wipe and wherein the wipe contains/is imbibed with at least one surfactant.

The expression "dry wipe" refers to a wipe having a water content of less than or equal to 7%, preferably 5%.

The wipe object of the present description allows application of the active principle on the skin following the application—by the user—of a reduced amount of water on the wipe itself at the time of use and rubbing of the wipe on the skin.

Thus, rubbing on the skin applies a pressure capable of breaking the microcapsules, resulting in leakage of the active principle (generally lipophilic) that is then emulsified in the aqueous phase (added at the moment of use by the user) by means of the surfactant contained in the wipe. The oil-in-water emulsion (O/W) thus formed allows the at least one active principle to exert its function, for example cleansing, moisturizing, etc., on the skin.

A particularly preferred embodiment concerns the use of lipophilic cosmetic active principles that can be emulsified during the application phase.

In a further embodiment, the microcapsules also contain a fragrance, which is released at the time of breakage and allows the user to perceive the activation of the microcapsules, i.e., release of the active principle.

Therefore, in a preferred embodiment the wipe object of the present description consists of an inert laminar support, in the form of a sheet of fabric or nonwoven fabric, on which are applied:
  i) a temperature stable surfactant;
  ii) a plurality of microcapsules containing the active principle(s), preferably lipophilic and optionally a fragrance (also preferably lipophilic).

In a particularly preferred embodiment also a film-forming agent is applied to the inert laminar support, capable of creating a film that traps and holds the microcapsules on the support itself.

In a preferred embodiment the wipe is composed of a sheet of nonwoven cotton fabric, synthetic material (e.g., polyester), or mixtures thereof, more preferably absorbent cotton, with reduced moisture content. In a still more preferred embodiment the wipe is composed of a layer of water-needled absorbent nonwoven cotton fabric. The wipe can be made natural or in various colours (white included) or combinations thereof.

Examples of lipophilic cosmetic active principles applicable on the wipe object of the present description are: oil- or triglyceride extracts of malva, chamomile, anise, fennel, carrot, aloe, orange, bamboo, calendula, fig, ginseng, St. John's wort, lavender, lemon, mandarine, apple, orchid, pine, tomato, propolis, rosemary, red grape, vanilla; oil of cashew, argan, avocado, babassu, borage, cocoa, carrot, cherry, coconut, canola, cotton, wheat germ, jojoba, linseed, macadamia nut, walnut husk, almond, neem, hazelnut, olive, palm, pine, grape seed, pistachio, musk rose.

Preferably the microcapsules used in the present invention are composed of polyurethane polymers, capable of resisting the manufacturing processes of the wipe. In particular, the microcapsules must be able to withstand without deterioration the drying and packaging processes necessary for realizing the dry wipe. In any case, microcapsules constituted of polyamide- or polyacrylate-based polymeric membranes can be used.

Examples of polyurethane polymers usable in the present invention are homo- and co-polymers of 2,4-toluene diisocyanate, 2,6-toluene diisocyanate, 4,4-diphenylmethane diisocyanate, 2,4-diphenylmethane diisocyanate, isophorone diisocyanate, methylene bis 4-cyclohexyl diisocyanate with hydroxyl compounds of tri-functional and/or difunctional amine compounds, among which ethylene glycol, diethylene glycol, propylene glycol, tetraethylene glycol, tripropylene glycol, 1,3-propanediol, 1,4-butanediol, neopentyl glycol, 1,6-hexanediol, 1,4-cyclohexanedimethanol, ethanolamine, methyldiethanolamine, phenyl diethanolamine, diethanolamine, glycerol, trimethylolpropane, 1,2,6-hexanetriol, triethanolamine, diethyltoluendiamine, dimethylthiotoluenediamine.

The polyurethane polymers are synthesized from isocyanates, which have as their main characteristic high reactivity of the isocyanate group —NCO with groups containing active hydrogen with which they form stable urethane compounds through exothermic reactions. Among the various isocyanates, the preferred compound is toluene diisocyanate (TDI) and in particular 2,4-toluene diisocyanate, which is more reactive than the 2,6-isomer. The order of reactivity of aromatic isocyanates with compounds containing active hydrogen is as follows: aliphatic amine>aromatic amine>primary hydroxyl>secondary hydroxyl>water>carboxylic acid=urea>urethane.

Microencapsulation is a technique known in the pharmaceutical, cosmetic, agricultural and food industries. It is realised through chemical and physical techniques, that is, emulsion, coacervation and interfacial polymerization techniques (chemical processes), spray-drying techniques, spray cooling and fluidized bed coating (physical processes).

Polyurethane-based microcapsules are preferably made by means of the interfacial polymerization technique; microcapsules based on polyamides can be obtained by means of the solvent spray-dry technique, while the emulsion technique can be used to make polyacrylate-based microcapsules.

The wipe and the phases of its industrial preparation comply with regulation CEN/TR15917:2009, which defines a cosmetotextile as a inert textile substrate capable of releasing cosmetic active principles over time and at the same time preserving them during the manufacturing, packaging, shipping and storage phases.

Indications for the realization of wipes according to the present description will now be provided by way of non-limiting example only. In particular, in the context of the present description we provide a specific example of interfacial polymerization because it is particularly advantageous for the coating/encapsulation of lipophilic active principles with polyurethane polymers.

Materials and Methods

A) Preparation of Absorbent Cotton (Inert Textile Substrate CEN/TR15917:2009):

Cotton flock, is a substance of vegetable origin, which—in the raw state—is in the form of fibre filaments grouped into tufts with the chemical composition shown in Table 1.

TABLE 1

| Compound | Quantity (%) |
| --- | --- |
| Cellulose | 83.5% |
| Fats and waxes | 0.8% |
| Pectin and lignin | 6.3% |
| Minerals and organic acids | 2.0% |
| hemicellulose and sugars | 0.5% |

TABLE 1-continued

| Compound | Quantity (%) |
|---|---|
| Miscellaneous | 0.4% |
| Water | 6.5% |

Thus the percentages of impurities (such as fats and waxes, pectin and lignin, minerals and organic acids) are very high, and give the fibre a lipophilic character that is removed through chemical processes of washing and sterilization known in the textile sector.

The raw cotton is then treated in an autoclave at 100° C. at a pressure of 3.5 bar for one hour as follows:

i) Washing with a solution as described in Table 2 using a ratio cotton:bath of 1:10.

TABLE 2

| Compound | Quantity (%) |
|---|---|
| Deionized water | 94.2% |
| Sodium laureth sulfate 27% w/w | 0.2% |
| Sodium polyacryiate MW/4500 | 0.2% |
| Caustic Soda 30% w/w | 1% |
| Hydrogen peroxide 130V | 1.5% |

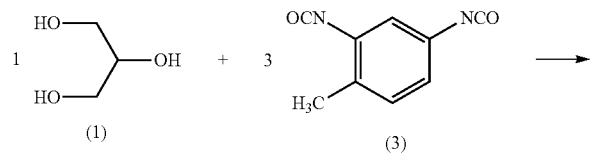

(1)     (3)

ii) Rinse with 3 cycles of water:
Time=10 min; Temperature=40° C., pressure=3.5 bar.

The resulting product is a white hydrophilic fibre flock and conforms to European Pharmacopoeia (Absorbent Cotton).

B) Preparation of a Nonwoven Textile Sheet of Absorbent Cotton (Inert Textile Substrate)

The resulting absorbent cotton flock is carded.

The carding is a process known in the textile sector that consists of opening, separating and cleaning the mass of fibres and their partial straightening.

Carding machines are composed of at least two large rollers, provided with metal teeth; reducing the distance between the rollers in subsequent steps produces a thin veil of fibres with a certain degree of parallelization.

The resulting fibre veil is interlaced by means of very high pressure jets of water (also known as water-needling) and air-dried in ovens between 100° and 150° C.

The resulting sheet is then cut into strips of various sizes.

C) Preparation of Polyurethane-based Microcapsules Containing Lipophilic Cosmetic Active Principles Microcapsules are made following known organic synthesis techniques for the preparation of a polyurethane-derived prepolymer by reacting a diisocyanate and a polyol.

The preparative phase consists of dissolving dimethylphenyl diisocyanate (MDI) or toluene diisocyanate (TDI) in cyclohexanone, heating the monomer to 80° C. and slowly adding the polyol, for example derivatives of polyethylene glycols, polypropylene glycols or glycerine, in molar concentrations of 3:1 for 1 hour.

The reaction of glycerin (1) with toluene diisocyanate (3) and the resulting polyurethane prepolymer (4) are schematically illustrated below.

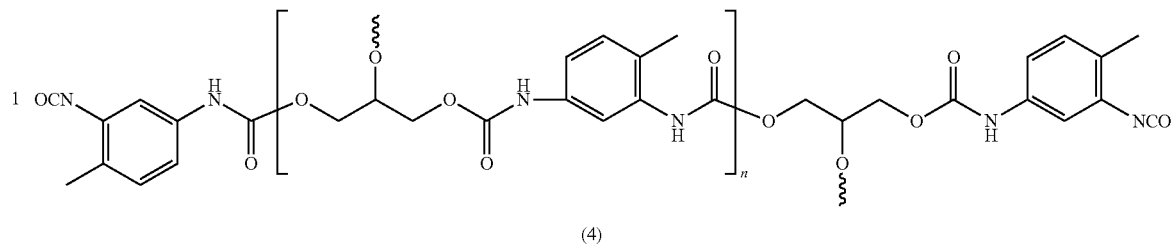

(4)

Subsequently, 30 ml of deionized water and 4.5 grams of gum arabic are mixed in a beaker at room temperature; the aqueous solution is stirred using a blade mixer for 2 hours.

Small amounts of a catalyst such as dibutyltin dilaurate are added to the prepolymer (4), made as described above.

The prepolymer (4) constitutes the oil phase (10 g), which is slowly added to the aqueous solution and the whole is agitated vigorously. Preferable, a 10% molar excess of other glycerine is added (in the aqueous solution) and the mixture is heated to 50° C. to lengthen the polymer chains, as shown schematically below:

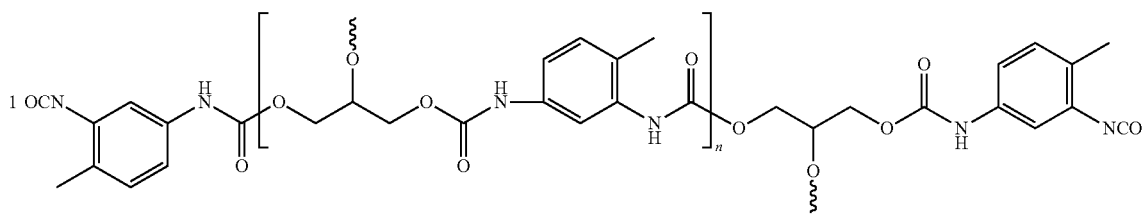

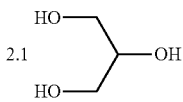

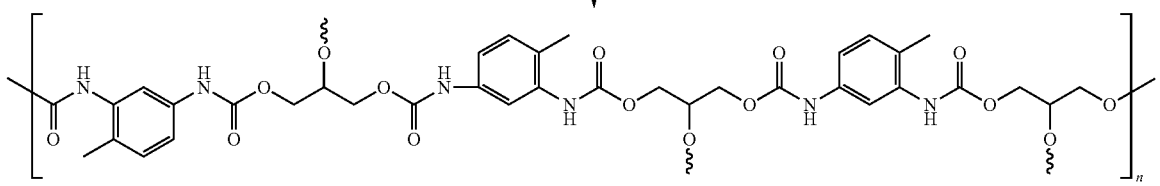

At 50° C. any free isocyanate is gradually eliminated through reaction with water, as illustrated schematically below:

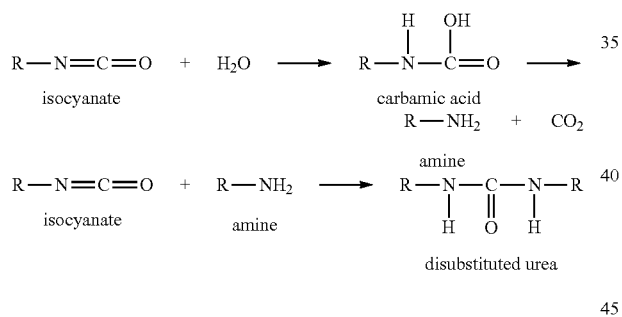

After an hour of agitation, a total of 2 grams of one or more cosmetic active principle, in this example carrot oil, a sunflower oil extract of aloe, vitamin E acetate and fragrance, in weight ratios of 40%:40%:10%:10% are added to the oil phase (constituted substantially by the polyurethane polymer).

The emulsion is stirred with a blade mixer for another two hours to complete the reaction, the microcapsules thus formed are collected and separated from the aqueous phase into a beaker, washed several times with deionized water and filtered.

The yield is greater than 90%.

C) Preparation of the Suspension of Polyurethane-based Microcapsules Containing Lipophilic Cosmetic Active Principles The microcapsules are then brought into suspension for subsequent application on the wipe.

The suspension is made using:

i) a fluid solvent, such as water or mixtures of water and alcohol;

ii) a film-forming agent, such as gum arabic, hydroxyl cellulose, carboxylated cellulose, acrylic and polyurethane polymers and copolymers, chitosan, polyvinyl alcohols;

iii) an anionic or nonionogenic or amphoteric surfactant. Preferred anionic surfactants are alcohols with linear and/or branched $C_{8-18}$ alkyl chains, sulfates and/or carboxylated or ethoxylated sulfates and/or carboxylates, in particular containing from 1 to 5 moles of ethylene oxide. The preferred nonionic surfactants are alcohols with linear and/or branched $C_{8-22}$ alkyl chains containing from 1 to 40 moles of ethylene oxide. The preferred amphoteric surfactants are the $C_{8-18}$ alkylbetaines, the $C_{8-18}$ alkylamido-betaines and $C_{8-18}$ alchylsulfo-betaines.

Particularly preferred surfactants are selected from lauryl ether sulfate, lauryl glucoside, cocamidopropyl betaine.

One litre of suspension was prepared by mixing very slowly with a magnetic stirrer, 680 ml, of cold deionized water and 20 g of carboxylated cellulose, 100 grams of an aqueous solution of cocamidopropyl betaine at 40% w/w and 200 grams of microcapsules containing carrot oil, sunflower oil extract of aloe, vitamin E acetate and fragrance.

E) Preparation of the Absorbent Nonwoven Cotton Sheet Loaded with the Suspension Containing the Microcapsules.

The following phase consists of spraying the suspension obtained as described above on a strip of absorbent cotton sheet.

The suspension is sprayed at between 5 and 30% by weight with respect to the absorbent cotton sheet, preferably between 10 and 15%.

The strip of absorbent cotton sheet is then dried in a hot air oven at a temperature comprised between 80 and 120° C.

Then the resulting strip of sheet material is cut and packaged to obtain dry wipes with a maximum water content of 5% as residual moisture in the materials used.

The invention claimed is:

1. A dry wipe for application of at least one active principle on skin, including:
   an inert laminar support;
   a plurality of microcapsules applied to the laminar support, the microcapsules containing the at least one active principle, and
   at least one surfactant applied to the laminar support,
   wherein the microcapsules are made of a polyurethane polymer,
   wherein the polyurethane polymer is made from:
   i) homopolymers of 2,4-toluene diisocyanate, 2,6-toluene diisocyanate, 4,4-diphenylmethane diisocyanate, 2,4-diphenylmethane diisocyanate, isophorone diisocyanate, or methylene bis 4-cyclohexyl diisocyanate, or
   ii) copolymers of 2,4-toluene diisocyanate, 2,6-toluene diisocyanate, 4,4-diphenylmethane diisocyanate, 2,4-diphenylmethane diisocyanate, isophorone diisocyanate, or methylene bis 4-cyclohexyl diisocyanate,
   wherein the i) homopolymers or the ii) copolymers are reacted with monomeric di- or tri- functional hydroxyl compounds,
   wherein the monomeric di- or tri- functional hydroxyl compounds are selected from:
   ethylene glycol, diethylene glycol, propylene glycol, tetraethylene glycol, tripropylene glycol, 1,3-propanediol, 1,4-butanediol, neopentyl glycol, 1,6-hexanediol, 1,4-cyclohexanedimethanol, glycerol, trimethylolpropane, and 1,2,6-hexanetriol, and
   wherein the dry wipe is constructed such that the at least one active principle is released by the microcapsules at a time of use by means of rupture of the microcapsules, and is emulsified in an aqueous phase added at the time of use by means of the surfactant, wherein the rupture of the microcapsules is realized through application of a pressure, and
   wherein the dry wipe is packaged in a unsealed package.

2. The dry wipe according to claim 1, wherein at least one active principle is a lipophilic active principle.

3. The dry wipe according to claim 1, wherein the surfactant is selected from: cocamidopropyl betaine, lauryl ether sulfate, and lauryl glucoside.

4. The dry wipe according to claim 1, wherein the dry wipe further comprises a film-forming agent applied on the laminar support.

5. The dry wipe according to claim 4, wherein the film-forming agent is selected from: gum arabic, hydroxycellulose, carboxylated cellulose, acrylic polymers and copolymers, polyurethane polymers and copolymers, chitosan, and polyvinyl alcohols.

6. The dry wipe according to claim 1, wherein the microcapsules also contain at least one fragrance.

7. The dry wipe according to claim 1, wherein the inert laminar support comprises a woven or nonwoven fabric.

8. The dry wipe according to claim 1, wherein the inert laminar support comprises cotton, synthetic materials, or mixtures thereof.

9. The dry wipe according to claim 1, wherein the inert laminar support is a sheet of absorbent cotton.

10. The dry wipe according to claim 1, wherein the microcapsules also contain at least one lipophilic fragrance.

11. The dry wipe according to claim 1, wherein the inert laminar support is a sheet of water-needled absorbent cotton.

12. The dry wipe according to claim 1, wherein the surfactant comprises:
    an alcohol with linear and/or branched $C_{8-18}$ alkyl chains, containing from 1 to 5 moles of ethylene oxide,
    a sulfate, containing from 1 to 5 moles of ethylene oxide, or
    a carboxylate, containing from 1 to 5 moles of ethylene oxide.

13. The dry wipe according to claim 1, wherein the surfactant comprises:
    an ethoxylated sulfate, containing from 1 to 5 moles of ethylene oxide, or
    an ethoxylated carboxylate, containing from 1 to 5 moles of ethylene oxide.

14. The dry wipe according to claim 1, wherein the surfactant comprises:
    an alcohol with linear or branched $C_{8-22}$ alkyl chains, containing from 1 to 40 moles of ethylene oxide.

15. The dry wipe according to claim 1, wherein the surfactant comprises:
    $C_{8-18}$ alkyl-betaine,
    $C_{8-18}$ alkylamido-betaine, or
    $C_{8-18}$ alkylsulfo-betaine.

* * * * *